US008168414B2

(12) United States Patent
Tzortzis et al.

(10) Patent No.: US 8,168,414 B2
(45) Date of Patent: May 1, 2012

(54) BETA-GALACTOSIDASE WITH TRANSGALACTOSYLATING ACTIVITY

(75) Inventors: Georgios Tzortzis, Reading (GB); Athanasios K Goulas, Reading (GB); Theodoros Goulas, Reading (GB)

(73) Assignee: Clasado Inc., Panama (PA)

( * ) Notice: Subject to any disclaimer, the term of this patent is extended or adjusted under 35 U.S.C. 154(b) by 92 days.

(21) Appl. No.: 12/225,626

(22) PCT Filed: Mar. 27, 2007

(86) PCT No.: PCT/GB2007/001081
§ 371 (c)(1),
(2), (4) Date: Oct. 27, 2008

(87) PCT Pub. No.: WO2007/110619
PCT Pub. Date: Oct. 4, 2007

(65) Prior Publication Data
US 2009/0117080 A1    May 7, 2009

(30) Foreign Application Priority Data

Mar. 28, 2006  (GB) .................................. 0606112.1

(51) Int. Cl.
*C12N 9/00* (2006.01)
*C07H 21/04* (2006.01)
(52) U.S. Cl. ...................................... 435/183; 536/23.2
(58) Field of Classification Search .................. 435/183; 536/23.2
See application file for complete search history.

(56) References Cited

U.S. PATENT DOCUMENTS

| 4,435,389 A | 3/1984 | Mutai et al. |
| 4,944,952 A | 7/1990 | Kobayashi et al. |
| 5,149,640 A | 9/1992 | Oonishi et al. |
| 5,294,546 A | 3/1994 | Dombou et al. |
| 2002/0086358 A1 | 7/2002 | Jorgensen et al. |
| 2008/0199444 A1 | 8/2008 | Cui |

FOREIGN PATENT DOCUMENTS

| AU | 2003294835 B2 | 6/2004 |
| EP | 0 089 940 A1 | 9/1983 |
| EP | 0 438 182 | 7/1991 |
| EP | 1 227 152 A1 | 7/2002 |
| GB | 2 412 380 B | 11/2005 |
| JP | 62059290 | 3/1987 |
| JP | 3049692 | 3/1991 |
| JP | 3049693 | 3/1991 |
| JP | 3246296 | 11/1991 |
| JP | 5-146273 | 6/1992 |
| JP | 5-146296 | 6/1993 |
| JP | 7089976 | 4/1995 |
| JP | 9121853 | 5/1997 |
| JP | 10023898 | 1/1998 |
| WO | WO 88/08025 | 10/1988 |
| WO | WO 96/06924 | 3/1996 |
| WO | WO 00/33854 A | 6/2000 |
| WO | WO 00/46345 | 8/2000 |
| WO | WO 01/90317 A2 | 11/2001 |
| WO | WO 2004/052121 A1 | 6/2004 |
| WO | WO 2004/074496 A1 | 9/2004 |
| WO | WO 2005/003329 | 1/2005 |
| WO | WO 2005/003329 A1 | 1/2005 |
| WO | WO 2007/054459 A2 | 5/2007 |
| WO | WO 2010/023422 A1 | 3/2010 |

OTHER PUBLICATIONS

Hung et al., Molecular and biochemical analysis of two beta-galactosidases from *Bifidobacterium infantis* HL96, Appl Environ Microbiol. 67(9):4256-63, 2001.*
Schell et al., The genome sequence of *Bifidobacterium longum* reflects its adaptation to the human gastrointestinal tract, Proc Natl Acad Sci U S A. 99(22):14422-7, 2002.*
Møller, Peter L. et al , "Intra- and Extracellular β-Galactosidases from *Bifidobacterium bifidum* and *B. infantis*: Molecular Cloning, Heterologous Expression, and Comparative Characterization", Applied and Environmental Microbiology, May 2001, vol. 67, No. 5, pp. 2276-2283.
Dumortier, Vincent et al., "Primary structure of ten galactosides formed by transglycosylation during lactose hyrolysis by *Bifidobacterium bifidum*", Carbohydrate Research, vol. 201, (1990), pp. 115-123.
Russel P., 2002 iGenetics, Pearson Education, Inc., San Francisco, pp. 187-189.
Paton, James C., et al. "Pathogenesis and Diagnosis of Shiga Toxin-Producing *Escherichia coli* Infections", Clinical Microbiology Reviews, Jul. 1998, vol. 11, No. 3, pp. 450-479.
Karlsson, Karl-Anders, "Animal Glycosphingolipids as Membrane Attachment Sites for Bacteria", Annual Reviews Bioch. 1989, vol. 58, pp. 309-350.
Lawson, Paul A. et al., "Recognition of *Fusobacterium nucleatum* subgroups Fn-1, Fn-2 and Fn-3 by ribosomal RNA gene restriction patterns", FEMS Microbiology Letters, 1989. vol. 65, pp. 41-46.
Krieg, P.A. et al., "In Vitro RNA Synthesis with SP6 RNA Polymerase", Methods in Enzymology. vol. 155, pp. 397-415 , 1987.
International Preliminary Report on Patentability and Written Opinion of the International Searching Authority dated Oct. 9, 2008, for corresponding International application No. PCT/GB2007/001081.
Sambrook J., et al., *Molecular Cloning: A Laboratory Manual*, vol. 3, Third Edition, (2002), Chapter 15, Expression of Cloned Genes in *Escherichia coli*, pp. 15.1-15.65 www.MolecularCloning.com.
International Search Report, dated Jul. 4, 2007, corresponding to PCT/GB2007/001081.
Written Opinion of the International Searching Authority, dated Jul. 4, 2007, corresponding to PCT/GB2007/0001081.
Møller, P.L. et al in Appl & Environ. Microbial., (2001), 62, (5), 2276-2283 (on Order).
Dumortier et al in Carbohydrate Research, 201, (1990), 115-123 (on Order).
J C and Paton, A W (1998), Clin. Microbiol. Revs., 11, 450-479; Carlsson, K A (1989), Ann. Reviews Biochem., 58, 309-350 (on Order).
Lawson et al. (1989) Fems Microbiol Letters, 65, (1-2), 41-45 (on Order).

(Continued)

*Primary Examiner* — Wu-Cheng Winston Shen
(74) *Attorney, Agent, or Firm* — Christie, Parker & Hale, LLP

(57) ABSTRACT

The present invention concerns a new β-galactosidase with transgalactosylating activity isolated from *Bifidobacterium bifidum*. The β-galactosidase is capable of converting lactose to a mixture of galactooligosaccharides which are β-linked and unexpectedly produces the α-linked disaccharide galactobiose. The mixture may be incorporated into numerous food products or animal feeds for improving gut health by promoting the growth of bifidobacteria in the gut, and repressing the growth of the pathogenic microflora.

3 Claims, 5 Drawing Sheets

OTHER PUBLICATIONS

Russel P., 2002 iGenetics, Pearson Education, Inc., San Francisco, 187-189 (on Order).
Sambrook J. and Russell W. D. (2001). Molecular Cloning: A Laboratory Manual. Cold Spring Harbor Laboratory Press, New York (on Order).
Krieg, P.A. and Melton, D.A. (1987). In vitro RNA synthesis with SP6 RNA polymerase. Methods in Enzymology. 155: 397-415 (on Order).
Sambrook J. Molecular Cloning: A Laboratory Manual (2002) (on Order).
Sambrook and Russell, 2001 (on Order).
Albersheim, et al., "A Method for the Analysis of Sugars in Plant Cell-Wall Polysaccharides by Gas-Liquid Chromatography", Carbohydrate Research, 5, 1967, pp. 340-345.
Blakeney, A.,et al., "A Simple and Rapid Preparation of Alditol Acetates for Monosaccharide Analysis", Carbohydrate Research, Elsevier Scientific Publishing Co., vol. 113 (1983) pp. 291-299.
Blanchette, D., et al., "α- and β-Galactosidase properites of Bifidobacterium infantis", Milchwissenschaft, vol. 47, No. 1, (1992), pp. 18-21.
Branden, et al., "Introduction to Protein Structure", Garland Publishing Inc., NY, pp. 247 (1991) (3 ppg attached).
Carpita, N., et al., "Linkage Structure of Carbohydrates by Gas Chromatography-Mass Spectrometry (GC-MS) of Partially Methylated Alditol Acetates", Analysis of Carbohydrates by GLC and MS, pp. 157-216, 1989.
Chabaud, et al., "Contribution of Interleukin 17 to Synovium Matrix Destruction in Rheumatoid Arthritis", Cytokine, vol. 12, No. 7, Jul. 2000, pp. 1092-1099.
Ciucanu, I., et al., "A Simple and Rapid Method for the Permethylation of Carbohydrates", Carbohydrate Research, 131 (1984) pp. 209-217, Elsevier Science Publishers.
Crittenden; R., "Prebiotics"; Probiotics: A Critical Review ISBN 1-898486-15-8; 1999 Horizon Scientific Press, Wymondham, U.K., pp. 141-156.
Database UniProt [Online] Nov. 1, 1999, "Alpha-galactosidase (EC 3.2.1.22)." XP002431984 retrieved from EBI accession No. UNIPROT:Q9XCX2; Database accession No. Q9XCX2, see sequence.
Database Geneseq [Online] Nov. 19, 2002, "Bifidobacterium longum NCC2705 ORF amino acid sequence SEQ ID No:919." XP002431983 retrieved from EBI accession No. GSP:ABP66175; Database accession No. ABP66175; see SEQ ID No: 919.
Database UniProt [Online] Sep. 27, 2005, "Glycoside hydrolase, clan GH-D." XP002431985 retrieved from EBI accession No. UNIPROT:Q40Z83; Database accession No. Q40Z83, see sequence.
Database UniProt [Online] Dec. 20, 2005, "Alpha-galactosidase (EC 3.2.1.22)." XP002431987 retrieved from EBI accession No. UNIPROT:Q2XQ11; Database accession No. Q2XQ11, see sequence.
Database UniProt [Online] May 30, 2006, "Alpha-galactosidase (EC 3.2.1.22)." XP002431986 retrieved from EBI accession No. UNIPROT:Q1KTD9; Database accession No. Q1KTD9, see sequence.
Database EMBL (Online) Oct. 26, 2000, "Bifidobacterium bifidum gene for beta-galactosidase (3701 bp)" 3 pages, XP002429539.
Database UniProt (Online) Mar. 1, 2001, "Beta-galactosidase (EC 3.2.1.23)." 1 page XP002429540.
Database EMBL (Online) Aug. 24, 2004, "Bifidobacterium breve B-galactosidase (B-gal) gene, complete cds" 2 pages.
Doares, Steven, et al., "An Improved Method for the Preparation of Standards for Glycosyl-linkage Analysis of Complex Carbohydrates", Carbohydrate Research, 210 (1991) pp. 311-317, Elsevier Science Publishers.
Dumortier, V., et al; "Purification and properties of α β-D-galactosidase from Bifidobacterium bifidum exhibiting a transgalactosylation reaction"; Biotechnol. Appl. Biochem. 19, pp. 341-354 (1994).
Gibson, G., et al., "Dietary Modulation of the Human Colonic Microbiota: Introducing the Concept of Prebiotics", Critical Review, American Institute of Nutrition, 1995, pp. 1401-1412.
Gibson; G. "Bifidobacteria and Oligosaccharides-The Functional Use of Prebiotics"; Positive Nutrition: Functional Foods; IBC Technical Services, London 1995, 34 pages.
Gibson; G., "Probiotics: New Developments in Functional Foods"; Chandos Publishing, Oxford 2000, 96 pages.
Gopal, P.K., et al., "Utilisation of galacto-oligosaccharides as selective substrates for growth by lactic acid bacteria including Bifidobacterium lactis DR 10 and Lactobacillus rhamnosus DR20," International Dairy Journal 11 (2001) pp. 19-25.
Goulas A et al: "Development of a process for the production and purification of α- and β-galactooligosaccharides from Bifidobacterium bifidum NCIMB 41171" International Dairy Journal, vol. 17, No. 6, Jun. 2007, pp. 648-656, XP002431977.
Hanatani, Mitsuya et al., "Physical and Genetic Characterization of the Melibiose Operon and Identification of the Gene Products in Escherichia coli"; The Journal of Biological Chemistry, Feb. 10, 1984, vol. 259, No. 3, pp. 1807-1812.
Hashimoto, H., et al., "Production of the Positional Isomers of α-Galactobiose by the Reverse Reaction of α-Galactosidase Candida guilliermondii H-404", Journal of Applied Glycoscience, vol. 48, No. 3, (2001), pp. 279-285.
Hashimoto, H., et al., "Candida guilliermondii H-404", Journal of Applied Glycoscience, vol. 41, No. 2, (1994), pp. 143-150 (includes English abstract).
Hung et al., "Molecular and Biochamical Analysis of Two Beta-Galactosidases from Bifidobacterium infantis, HL96, Appin Environ Microbiol. 67(9)" 4256-63, 2001.
Ito, et al.; "Effects of Administration of Galactooligosaccharides on the Human Faecal Microflora, Stool Weight and Abdominal Sensation"; Microbial Ecology in Health and Disease, vol. 3:285-292 (1990).
Ito, et al.; "Effects of Transgalactosylated Disaccharides on the Human Intestinal Microflora and Their Metabolism"; J. Nutr. Sci. Vitaminol., 39, 279-288, 1993.
Lamoureux L et al: "Production of Oligosaccharides in Yogurt Containing Bifidobacteria and Yogurt Cultures" Journal of Dairy Science, American Dairy Science Association, Savoy, IL, US, vol. 85, No. 5, May 2002, pp. 1058-1069, XP001124200; ISSN: 0022-0302 the whole document, in particular Table 5.
MacCormick, C.A., et al., "Characterization of a Variant of the Polysaccharide Acetan Produced by a Mutant of AcetobacterXylinum Strain CR1/4", Journal of AppliedBacteriology 1993, 74, pp. 196-199.
MacFarlane, G., et al., "Validation of a Three-Stage Compound Continuous Culture System for Investigating the Effect of Retention Time on the Ecology and Metabolism of Bacteria in the Human Colon", Microbial Ecology, 1998, 35:180-187.
Matsumoto et al., "Galactooligosaccharides", Japanese Technology Reviews, Section E, Chapter 5, vol. 2.3, 1993, pp. 90-94 (9 sheets).
Olano-Martin, E., et al; "Pectins and Pectic-oligosaccharides inhibit Escherichia coli O157:H7 Shiga toxin as directed towards the human colonic cell line HT29"; FEMS Microbiology Letters 218 (2003), pp. 101-105.
Onishi, N., et al; "Production of Galacto-Oligosaccharide from Lactose by Sterigmatomyces elviae CBS8119", Applied and Environmental Microbiology, Nov. 1995, pp. 4022-4025.
Palframan, et al., "Carbohydrate Preferences of Bifidobacterium Species Isolated from the Human Gut", Current Issues in Intestinal Microbiology, vol. 4, 2003, pp. 71-75.
Prenosil, J.E., et al; "Formation of Oligosaccharides during Enzymatic Lactose: Part 1: State of Art"; Biotechnology and Bioengineering, vol. 30, pp. 1019-1025 (1987).
Rabiu, B., et al; "Synthesis and Fermentation Properties and Novel Galacto-Oligosaccharides by β-Galactosidases from Bifidobacterium Species"; Applied and Environmental Microbiology, Jun. 2001, pp. 2526-2530.
Rowland et al., "The effects of transgalactosylated oligosaccharides on gut flora metabolism in rats associated with a human faecal microflora", Journal of Applied Bacteriology, 1993, 74, pp. 667-674.
Sako, T., et al; "Recent progress on research and applications of non-digestible galacto-oligosaccharides"; International Dairy Journal 9 (1999), pp. 69-80.
Scalabrini P. et al:, "Characterization of Bifidobacterium Strains for Use in Soymilk Fermentation" International Journal of Food Microbiology, Elsevier Science Publishers, Amsterdam, NL, vol. 39, No. 3, 1998, pp. 213-219, XP000952364, ISSN: 0168-1605 the whole document, in particular Table 1.

Seffernick, et al., "*Melamine Deaminase and Atrazine Chlorohydrolase: 98 Percent Identical but Functionally Different*", Journal of Baceteriology, vol. 183(8):2408-2410, 2001.

Smeianov et al., GenBAnk accession No. AAG02023, 2000.

Sweet, David, et al., "*Quantitative Analysis by Various G.L.C. Response-Factor Theories for Partially Methylated and Partially Ethylated Alditol Acetates, Carbohydrate Research*", 40 (1975) pp. 217-225, Elsevier Science Publishers.

Tanaka, R., et al; "*Effects of Administration of TOS and Bifidobacterium breve 4006 on the Human Fecal Flora*"; Bifidobacteria microflora, vol. 2(1), 17-24, 1983.

Tzortzis, G., et al: "*Synthesis of prebiotic galactooligosaccharides using whole cells of a novel strain, Bifidobacterium bifidum NCIMB 41171" Applied Microbiology and Biotechnology*", Springer-Verlag, BE, vol. 68, No. 3, Aug. 1, 2005, pp. 412-416, XP019331926; ISSN: 1432-0614.

Van Den Broek. L A M, et al: "*Synthesis of alpha-galacto-oligosaccharides by a cloned alpha-galactosidase from Bifidobacterium adolescentis*" Biotechnology Letters, vol. 21, No. 5, May 1999, pp. 441-445, XP009083120; ISSN: 0141-5492 the whole document, in particular p. 443, left-handed col., last paragraph.

Van Laere K, M J, et al: "*Transglycosidase activity of Bifidobacterium adolescentis DSM 20083 alpha-galactosidase*" Applied Microbiology and Biotechnology, Springer Verlag, Berlin, DE, vol. 52, No. 5, Nov. 1999 pp. 681-688, XP002285615; ISSN: 0175-7598 the whole document.

Van Laere , K.,et al; "*Characterization of a Novel β-Galactosidase from Bifidobacterium adolescentis DSM 20083 Active towards Transgalactooligosaccharides*", Applied and Environmental Microbiology, Apr. 2000, pp. 1379-1384.

Witowski, et al., "*Converstion of α β-Ketoacyl Synthase to a Malonyl Decarboxylase by Replacement of the Active-Site Cystein with Glutamine*", Biochemistry 38:11643-11650 (1999).

Yuan, et al., "*Feruloyl oligosaccharides stimulate the growth of Bifidobacterium bifidum*", Anaerobe, vol. 11, 2005, pp. 225-229.

Zarate, S., et al; "*Oligosaccharide Formation During Enzymatic Lactose Hydrolysis: A Literature Review*"; Journal of Food Protection, vol. 53, No. 3, pp. 262-268 (Mar. 1990).

Ziggers, D., "*TOS, a new prebiotic derived from whey*," Feed Mix, vol. 9, No. 6, 2001, pp. 7-9.

International Search Report for PCT/GB2004/002815 dated Jul. 12, 2004.

International Search Report dated Jun. 11, 2007, corresponding to PCT/GB2006/004796, 5 sheets.

International Search Report, dated May 14, 2007, corresponding to PCT/GB2007/000178.

Written Opinion of the International Searching Authority, dated May 14, 2007, corresponding to PCT/GB2007/000178.

Japanese Office Action dated Dec. 9, 2008, in corresponding Japanese Patent Application No. 2006-500267, along with English translation.

U.S. Office Action dated Oct. 20, 2010 for U.S. Appl. No. 12/086,834.

U.S. Office Action dated Oct. 6, 2009 for U.S. Appl. No. 10/552,483.

U.S. Notice of Allowance dated Oct. 28, 2010 for U.S. Appl. No. 10/552,483.

International Search Report and Written Opinion dated May 18, 2007 for International Application No. PCT/EP2006/068029 (9 sheets).

International Preliminary Report on Patentability dated May 14, 2008 for International Application No. PCT/EP2006/068029 (7 sheets).

International Search Report and Written Opinion dated Sep. 4, 2009 for International Application No. PCT/GB2009/001302 (9 sheets).

U.S. Office Action dated Dec. 6, 2010 for U.S. Appl. No. 12/223,508 (18 sheets).

U.S. Office Action dated Feb. 15, 2011 for U.S. Appl. No. 12/084,681 (27 sheets).

An, et al, "*Isolation of Phaffia rhodozyma Mutants with Increased Astaxanthin Content*", Applied and Environmental Microbiology, vol. 55, No. 1, Jan. 1989, pp. 116-124.

U.S. Notice of Allowance dated Feb. 24, 2011 for U.S. Appl. No. 12/086,834 (5 sheets).

U.S. Notice of Allowance dated May 27, 2011 for U.S. Appl. No. 12/223,508 (8 sheets).

U.S. Notice of Allowance dated Aug. 4, 2011 for U.S. Appl. No. 12/086,834 (10 sheets).

International Search Report and Written Opinion of the International Searching Authority, mailed Jan. 13, 2010, issued to Application No. PCT/GB2009/001329, 10 pages.

International Search Report and Written Opinion of the International Searching Authority, mailed Jun. 23, 2010, issued to Application No. PCT/GB2010/050659, 9 pages.

Gibson, et al., "Dietary modulation of the human colonic microbiota: updating the concept of prebiotics" Nutrition Research Reviews, vol. 17, No. 2, Dec. 1, 2004, pp. 259-275, XP009117209.

Searle, et al., "A mixture containing galactooligosaccharide, produced by the enzymatic activity of Bifidobacterium bifidum, reduces Salmonella enterica serovar Typhimurium infection in mice" Journal of Medical Microbiology, vol. 58, No. 1, Jan. 2009, pp. 3748, XP002560309.

Tzortzis, et al., "A-novel galactooligosaccharide mixture increases the bifidobacterial population numbers in a continuous in vitro fermentation system and in the proximal colonic contents of pigs in vivo" Journal of Nutrition, vol. 135, o. 7, Jul. 2005, pp. 1726-1731, XP002560310.

Vulevic, et al., "Modulation of the fecal microflora profile and immune function by a novel trans-galactooligosaccharide mixture (B-GOS) in healthy elderly volunteers, " Am J Clin Nutr 2008;88:1438-46. Printed in USA. © 2008 American Society for Nutrition.

* cited by examiner

Figure 1

```
   1 tcctttagat tggattgaaa acttcctttt tttatgtaaa aggatattcg gggaaattcc
  61 cttttgaaa atttcatgac caaaaatccc cttaacgtga gttttcgttc cactgagcgt
 121 cagaccccgt agaaaagatc aaaggatctt cttgagatcc ttttttctg cgcgtaatct
 181 gctgcttgca aacaaaaaaa cccccgctac cagcggtggt ttgtttgccg gatcaagagc
 241 taccaactct ttttccgaag gtaactggct tcagcagagc gcagatacca aatactgttc
 301 ttctagtgta gccgtagtta ggccaccact tcaagaactc tgtagcaccg cctacatacc
 361 tcgctctgct aatcctgtta ccagtggctg ctgccagtgg cgataagtcg tgtcttaccg
 421 ggttggactc aagacgatag ttaccggata aggcgcagcg gtcgggctga acggggggtt
 481 cgtgcacaca gcccagcttg gagcgaacga cctacaccga actgagatac ctacagcgtg
 541 agctatgaga aagcgccacg cttcccgaag ggagaaaggc ggacaggtat ccggtaagcg
 601 gcagggtcgg aacaggagag cgcacgaggg agcttccagg gggaaacgcc tggtatcttt
 661 atagtcctgt cgggtttcgc cacctctgac ttgagcgtcg attttgtga tgctcgtcag
 721 gggggcggag cctatggaaa aacgccagca acgcggcctt tttacggttc ctggcctttt
 781 gctggccttt tgctcacatg ttctttcctg cgttatcccc tgattctgtg gataaccgta
 841 ttaccgcctt tgagtgagct gataccgctc gccgcagccg aacgaccgag cgcagcgagt
 901 cagtgagcga ggaagcggaa gagcgcccaa tacgcaaacc gcctctcccc gcgcgttggc
 961 cgattcatta atgcaggtta acctggctta tcgaaattaa tacgactcac tataggggaga
1021 ccggcagatc tgatatcatc gatgaattcg agctcggtac ccggggatcc tctagagtcg
1081 acctgcagaa gtactggcag tccggcctcg ccgccggcgc cgtcaaggag tgatctcgcg
1141 ggagggccag tgtccgcttg cagcatgcgt cacgttcgtc tgacggtctt gacgtgcgcc
1201 tagcggctgg ccctccctac ggaacatgta tatgatatgg agggacgctc accgtgtgcg
1261 atgcgggctg gcgcgatatg gcaccagccc gcatcgcatg tcacagttga tttttcgtcg
1321 atgcgacggt tcggccgggg cgtcagacaa tgaacaagta atggagcgga atatgagtaa
1381 acgcagaaag cacagttggc cgcagccgct gaagggcgcc gaatcccgtc tctggtatgg
1441 cggtgattac aatcccgacc aatgccgga ggaggtctgg gacgatgata tccgtctgat
1501 gaagaaggcc ggcgtcaacc ttgtatcagt cggcatcttc tcatgggcga agatcgagcc
1561 ggaggaaggc aagtacgatt tcgactggct ggaccgtgcc atcgataagc tcggcaaggc
1621 gggcatcgct gtagacctcg cctccgccac cgcctcccg ccgatgtggc tgacccaggc
1681 ccatccggag gtgctgtgga aggacgagcg cggcgacacc gtgtggccgg gtgcccgtga
1741 gcattggcgt ccgacgagcc ctgtgttccg cgagtacgcg ctgaacctgt gccgtcgtat
1801 ggccgagcac tataagggca acccatacgt ggtggcctgg cacgtgagca acgaatacgg
1861 ctgccacaac cgcttcgact actcggacga cgccatgcgc gccttccaga gtggtgcaa
1921 gaagcgctac aagaccatcg acgcggtgaa cgaggcctgg ggaacagcgt ctgggccca
1981 gcacatgaac gatttctccg agatcatccc gcctcgctac atcggtgacg gcaacttcat
2041 gaacccgggc aagctgctcg actacaagcg gttcagctcc gacgcgctca aggagctcta
2101 catcgccgaa cgtgacgtgc tggagtccat cacgccgggt ctgccgctga ccaccaattt
2161 catggtgtct gccggcggct cgatgcttga ctatgacgac tggggtgcgg aggtcgattt
2221 cgtctccaac gaccactact tcacgccggg cgaggaccat ttcgacgagg ttgcgtacgc
2281 cgcgtcgctg atggacggca tttcacgcaa ggaaccgtgg ttccagatgg agcattccac
2341 ctccgcggtg aattggcgtc cgatcaacta ccgtgcggag ccgggctcgg tcgtgcgcga
2401 ctccctcgcg caggtcgcta tgggcgccga tgccatctgc tatttccagt ggcgacagtc
2461 caaggccggc gcggagaagt ggcactcctc gatggtgccg catgcgggcg aggattcgca
2521 gatcttccgt gatgtgtgcg agctgggcgc cgatctggga cgtctgtccg acgagggtct
2581 gatgggcacc aagacggtca agtccaaggt cgccgtcgtg ttcgactacg agtcccagtg
2641 ggccaccgag tacaccgcga acccgaccca gcaggtcgat cattggaccg agccgttgga
```

Figure 1 (continuation)

```
2701 ttggttccgc gcgcttgccg acaacggcat caccgccgac gtggttccgg tgcggtccga
2761 ttgggattcc tacgagattg ccgtgctgcc gtgcgtgtat ttgctgtccg aagagacgag
2821 ccgcagggtt cgggagttcg tggcgaacgg cggcaagttg ttcgtgacgt actacaccgg
2881 attgagcgac gagaacgacc acatctggct tggcggctac ccggggctcga ttcgtgacgt
2941 cgtcggcgtg cgcgtcgaag agttcgcccc gatgggcaac gacatgccgg gcgcattgga
3001 tcacctcgac ctggacaatg gcacggtggc gcatgacttt gccgacgtga tcacgtccac
3061 ggccgacacg tccacggtac tggcctccta taaggcggaa cgctggaccg gcatgaacga
3121 ggtgccggcc atcgtggcca acgggtatgg cgacgggcgg accgtatatg tcggatgccg
3181 tctgggccgt caggggcttg cgaagagcct gccggcgatg ctgggttcca tggggctgtc
3241 ggacctcgcc ggtgatggcc gcgtgctgcg tgtcgaacgc gccgacgccg cggcggcgag
3301 ccgcttcgag ttcgtgttca accgcaccca tgaaccggtg accgtcgacg ttgaagggga
3361 ggccatcgcg gcttcgctcg cgcatgtcga cgacgggcgg gccaccatcg atccgacggg
3421 tgttgtcgtg ctcaggcgat aatcgttgga aacactgggc tgtaagggct taggaaaggc
3481 gtatgtttgc ggtgacacgc gacatacgcc ttatgggaaa gaaggcgctg gcgcttaccg
3541 ggctgcggcg atgctggtca gcgtcgctgc gtgcggcaac tcaagcagca gctccgctcc
3601 gaagcaggaa ggcgacgtca aggaaatcac cgtgtgggct tggggcctac gctgactcag
3661 gtggccaagg acttcaaaaa aggagaccgg catcaatgtc aacctggtga acaccggcca
3721 gggcgacaag acctgggacg agttctatca ggacgccaag aagattcaca cccttggcga
3781 caactactac atcacgtccg acaccggtgt cgccggcttc tacgactcga tgacctggct
3841 ggccagtgcg acgctgttct ccaccgaagg cgagacggtc accattaacc tgactggcgc
3901 cccgaaggtc aaggcccgcg gtatcttcgg cgactacctt ggcaagtcct acaccggcaa
3961 ccagaagctg agcgatggcg tcgccgcttt gggaacaggc tctgaaggac tacgcgaagg
4021 atcagggcta caccgtcaag taaccttcgc agtcaagcaa tctggcgtgg taatgaccgg
4081 aatacggtga ccttcggtca tcccttcctc gtgtgaaggc ccctcccctc aacagggagg
4141 ggccttcaca tatctgcccc tgttgcaacg cgcgtgtaaa ctctacgatg agcgaattct
4201 tcccgacaca tcgagcacgc taaggagatg acatgacgat atcggcacgg ttgtggcggc
4261 tgcacctgca tatctttgtg ttgctcaaga tctgtgagat gacactggca gcacgcctcc
4321 agcgcgccgc cggacacgcg caccctcatc accgaatgga cggggggacca tatcatgacg
4381 actctgatcg ccaat
```

Figure 2

MYMIWRDAHRVRCGLARYGTSPHRMSQLIFRRCDGSAGASDNEQVMERNMSK
RRKHSWPQPLKGAESRLWYGGDYNPDQWPEEVWDDDIRLMKKAGVNLVSV
GIFSWAKIEPEEGKYDFDWLDRAIDKLGKAGIAVDLASATASPPMWLTQAHP
EVLWKDERGDTVWPGAREHWRPTSPVFREYALNLCRRMAEHYKGNPYVVAWH
VSNEYGCHNRFDYSDDAMRAFQKWCKKRYKTIDAVNEAWGTAFWAQHMNDFS
EIIPPRYIGDGNFMNPGKLLDYKRFSSDALKELYIAERDVLESITPGLPLTT
NFMVSAGGSMLDYDDWGAEVDFVSNDHYFTPGEDHFDEVAYAASLMDGISRK
EPWFQMEHSTSAVNWRPINYRAEPGSVVRDSLAQVAMGADAICYFQWRQSKA
GAEKWHSSMVPHAGEDSQIFRDVCELGADLGRLSDEGLMGTKTVKSKVAVVF
DYESQWATEYTANPTQQVDHWTEPLDWFRALADNGITADVVPVRSDWDSYEI
AVLPCVYLLSEETSRRVREFVANGGKLFVTYYTGLSDENDHIWLGGYPGSIR
DVVGVRVEEFAPMGNDMPGALDHLDLDNGTVAHDFADVITSTADTSTVLASY
KAERWTGMNEVPAIVANGYGDGRTVYVGCRLGRQGLAKSLPAMLGSMGLSDL
AGDGRVLRVERADAAAASRFEFVFNRTHEPVTVDVEGEAIAASLAHVDDGRA
TIDPTGVVVLRR

BETA-GALACTOSIDASE WITH TRANSGALACTOSYLATING ACTIVITY

CROSS-REFERENCE TO RELATED APPLICATION

This application is a National Phase Patent Application of International Application Number PCT/GB2007/001081, filed on Mar. 27, 2007, which claims priority of British Patent Application Number 0606112.1, filed on Mar. 28, 2006.

INCORPORATION BY REFERENCE

The material in the text file entitled "SEQLIST-ING12225626", amended Jan. 20, 2011 and being 12,200 bytes in size, is herein incorporated by reference in its entirety.

The present invention relates to a new β-galactosidase with transgalactosylating activity capable of converting lactose to a mixture of galactooligosaccharides. In particular it relates to a β-galactosidase isolated from a recently discovered strain of *Bifidobacterium bifidum*.

The invention particularly relates to DNA sequences encoding the isolated new β-galactosidase enzyme, to the enzyme encoded by such a DNA sequence and to a host cell comprising the DNA sequence or containing a recombinant vector incorporating the DNA sequence. The invention also relates to the use of the enzyme encoded by a DNA sequence, or of the host cell containing a DNA sequence or recombinant vector, to produce galactooligosaccharides.

Bifidobacteria naturally colonise the lower intestinal tract, an environment which is poor in mono and disaccharides since such sugars are preferentially consumed by the host and microbes present in the upper intestinal tract. In order to survive in the lower intestinal tract bifidobacteria produce various kinds of exo- and endoglycosidases in surface bound and/or extracellular forms, by which they can utilise diverse carbohydrates.

Besides hydrolase activity, some enzymes from bifidobacteria show transferase activity. This transglycosylation activity of glycosidases is extensively used for the enzymatic synthesis of various oligosaccharides, which have proven to act as bifidobacteria growth promoting factors.

It is known that members of bifidobacteria produce β-galactosidase enzymes that are involved in the bacterial metabolism of lactose. Møler, P. L. et al in *Appl & Environ. Microbial.*, (2001), 62, (5), 2276-2283 describe the isolation and characterisation of three β-galactosidase genes from a strain of *Bifidobacterium bifidum*. They found that all three β-galactosidases were able to catalyse the formation of beta-linked galactooligosaccharides by transgalactosylation.

Dumortier et al in *Carbohydrate Research*, 201, (1990), 115-123 described the formation of beta-linked oligosaccharides by a transgalactosylation reaction during lactose hydrolysis with *Bifidobacterium bifidum* DSM 20456. Their analysis of the structure of the mixture of oligosaccharides produced showed that the linkages were β-(1→3), β-(1→6) and β-(1→4)-D-galactosyl linkages. Dumortier suggested that compounds produced by *Bifidobacterium bifidum* are involved in the adherence of bacteria in the large intestine.

WO 01/90317 describes a new β-galactosidase from *Bifidobacterium bifidum*, in particular a truncated version of the enzyme that has a high transgalactosylating activity.

A strain of *Bifidobacterium bifidum* has been found that is capable of producing a galactosidase enzyme activity that converts lactose to a novel mixture of galactooligosaccharides which unexpectedly contains up to 35% of disaccharides including galabiose (Gal (α1-6)-Gal). This disaccharide is known (see Paton, J C and Paton, A W (1998), *Clin. Microbiol. Revs.*, 11, 450-479; Carlsson, K A (1989), *Ann. Reviews Biochem.*, 58, 309-350) to be an antiadhesive capable of preventing the adhesion of toxins, eg Shiga toxin and pathogens such as *E. coli*, to the wall of the gut.

This strain of *B bifidum* was deposited under accession number NCIMB 41171 at the National Collection of Industrial & Marine Bacteria, Aberdeen, UK on 31 Mar. 2003. It is also described in UK Patent No 2 412 380.

It has now been found that this strain of *B bifidum* produces several β-galactosidases, including a novel β-galactosidase. This enzyme produces a number of different oligosaccharides which are β-linked.

According to the invention there is provided a DNA sequence which encodes a protein with an amino acid sequence as given in SEQ. ID NO: 2 or hybridises under stringent conditions to the DNA sequence which encodes this protein. The DNA sequence is given in SEQ. ID NO: 1 or may comprise a fragment or degenerative thereof.

The phrase "degenerative" is construed to mean a DNA sequence which is at least 50% homologous to SEQ ID NO: 1, preferably from 50 to 98% homologous, most preferably from 75 to 95% homologous.

Such a DNA sequence may comprise nucleotide substitutions, additions or deletions which result in less than 60%, preferably less than 45%, more preferably less than 25% change in the amino acid sequence shown in SEQ. ID NO: 2. Nucleotide substitutions may result in conservative amino acid substitutions.

According to a second aspect of the invention there is provided an enzyme encoded by a DNA sequence as defined above. Such an enzyme may comprise the amino acid sequence given in SEQ. ID NO: 2 or a fragment thereof.

According to a third aspect of the invention there is provided a recombinant vector, preferably an expression vector, comprising a DNA sequence as defined above. Such a vector may be incorporated into a host cell such as a bacterial, yeast or fungal cell. Alternatively, the DNA sequence may be incorporated into such a host cell. A suitable host cell may be selected from the group comprising *Bifidobacterium, Lactococcus, Lactobacillus, Bacillus* for example *Bacillus subtilus* or *Bacillus circulans, Escherichia* and *Aspergillus* for example *Aspergillus niger*.

Using lactose as a substrate, the enzyme encoded by the DNA sequence as defined above produces a mixture of oligosaccharides, comprising disaccharides, such as Gal (β1-3) Glc, Gal (β1-3) Gal, Gal (β1-6) Gal and Gal (α1-6) Gal, trisaccharides and tetrasaccharides such as Gal (β31-6) Gal (β1-4) Glc, Gal (β1-3) Gal (β1-4) Glc and Gal (β1-6) Gal (β1-6) Gal (β1-4) Glc The enzyme or the host cell as described above may be used to produce a mixture of galactooligosaccharides which may form part of a product for improving gut health. Such a product may be selected from the group consisting of dairy products (for example liquid milk, dried milk powder such as whole milk powder, skimmed milk powder, fat filled milk powders, whey powders, baby milks, baby formula, ice cream, yoghurt, cheese, fermented dairy products), beverages such as fruit juice, infant foods, cereals, bread, biscuits, confectionery, cakes, food supplements, dietary supplements, animal feeds, poultry feeds or indeed any other food or beverage. The presence of galactooligosaccharides in such products has the advantage of enhancing the growth of health-promoting *Bifidobacterium* in the product or in the intestinal flora of the consumer after intake of the product or both.

Alternatively, the oligosaccharides so produced may be used for the preparation of a medicament, for example in tablet or capsule form, for preventing the adhesion of pathogens or toxins produced by pathogens to the gut wall. The medicament may be administered to a patient, for example following a course of antibiotic treatment, which often alters or even destroys the normal healthy gut flora.

According to yet a further aspect of the invention there is provided a process for producing an enzyme as defined above which comprises culturing a host cell as defined above in a suitable culture medium under conditions permitting expression of the enzyme and recovering the resulting enzyme or enzyme products from the culture.

The invention is also directed to a process for producing the mixture of galactooligosaccharides which comprises contacting the enzyme as defined above with a lactose-containing material under conditions that lead to the formation of the galactooligosaccharide mixture.

Suitable lactose containing material may be selected from commercially available lactose, whole milk, semi-skimmed milk, skimmed milk, whey, fat-filled milk and whey permeate. Such milk products may be obtained from cows, buffaloes, sheep or goats. Fat-filled milk is defined as whole milk that has been skimmed to remove the dairy fat, which is subsequently replaced by the addition of vegetable fat or oil.

BRIEF DESCRIPTION OF THE DRAWINGS

FIG. 1 shows the nucleotide sequence (SEQ. ID NO: 1) of Bifidobacterium bifidum β-galactosidase of the invention; and FIG. 2 shows the amino acid sequence (SEQ. ID NO: 2) corresponding to the nucleotide sequence of FIG. 1.

Figure 3:
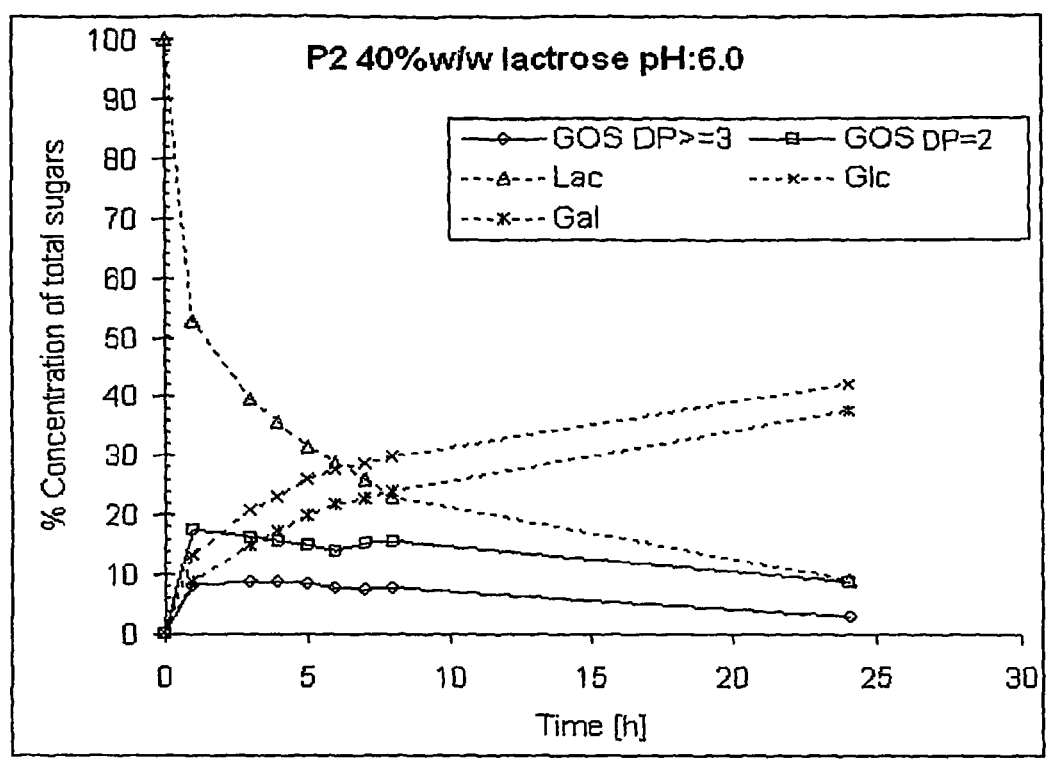
FIG. 3 is a graph showing the time course reaction during galactooligosaccharide synthesis with β-galactosidase and 40% (w/w) lactose in O.1 M phosphate buffer at pH 6.0 as substrate.

Genomic DNA was isolated from the Bifidobacterium bifidum strain (NCIMB 41171) using the method of Lawson et al. (1989) Fems Microbiol Letters, 65, (1-2), 41-45. The DNA was digested with restriction enzymes and fragments having a maximum size of 15 kbp were ligated with pSP72 vector which had been digested with the same restriction enzymes. E. coli cells were transformed with a vector containing insertions consisting of PstI, Eco RI, Bam HI, KpnI, SmaI or HindIII digested chromosomal DNA from the B. bifidum. Clones with β-galactosidase activity were selected on Luria Bertani agar plates containing p-nitrophenyl, X-β-Gal (5-bromo-4-chloro-3-indolyl-β-D-galactoside) and isopropyl-β-D-thiogalactoside (IPTG). Ligation mixtures with Pst I chromosomal DNA gave rise to thirteen β-galactosidase positive clones, one of which is identified as pP2.

DNA sequencing of the inserted DNA fragment P2 was performed using the dideoxy chain-termination method of Sanger (Russel P., 2002 iGenetics, Pearson Education, Inc., San Francisco, 187-189) using the BigDye Terminator V.3.O cycle sequencing kit (Applied Biosystems, USA). The DNA sequence of P2 is shown in FIG. 1 (SEQ. ID NO: 1).

The open reading frame (ORF) was located by using the ORF finder from NCBI (National Center of Biotechnology Information). The nucleotide sequence of FIG. 1 was translated in all six possible reading frames and one open reading frame of 738 amino acids encoding a putative β-galactosidase was identified. The translation is shown in FIG. 2 (SEQ. ID NO: 2).

The present invention will be further described by way of reference to the following example.

EXAMPLE 1

Materials and Methods

All chemicals and media preparations used throughout this study were obtained from Sigma (Dorset, UK), Invitrogen (Paisley, UK), Oxoid (Basingstoke, UK), Qiagen (West Sussex, UK) and Promega (Southampton, UK).

Bacterial Strains

The Bifidobacterium bifidum strain (NCIMB 41171) was maintained on cryogenic beads in Microbank tubes at −70° C. For later experiments, the strain was revived on Wilkinson Chalgren (WC) agar (Oxoid, UK) and TPY medium (trypticase phytone yeast extract medium) and grown anaerobically ($CO_2$ and $N_2$ composition 80% and 20% respectively) at 37° C. for 48 hours. The colony morphology and the absence of contamination were tested by gram staining.

E. coli Strains

Escherichia coli strain DH5a used in this study was commonly incubated under aerobic conditions at 37° C. in Luria Bertani (LB) agar or broth (Sambrook J. and Russell W. D. (2002). Molecular Cloning: A Laboratory Manual. Cold Spring Harbor Laboratory Press, New York) and when necessary was supplemented with antibiotics (100 μg/ml ampicillin and/or 15 μg/ml chloramphenical) and 40 μl of 2% X-β-Gal, 7 μl of 20% (isopopyl-β-D-thiogalactoside) IPTG which were applied on the surface of a pre-made 90 mm agar plate.

E. coli DH5a strain (Invitrogen, Paisley, UK) (genotype: F$^-$ φ 80lacZΔM Δ(lacZYA-argF)U169 recA1 endA1 hsdr17 ($r_k^-$, $m_k^-$)phoA supE44 thi-1 gyrA96 relA1λ$^-$) is an α-galactosidase positive strain and was used in expression experiments and for other genetic manipulations.

Genomic DNA Extraction from Bifidobacterium bifidum

Genomic DNA was isolated from the Bifidobacterium bifidum strain (NCIMB 41171) using the following method in which chromosomal DNA was prepared from cell pellet harvested from 100 ml of WC anaerobe broth. The cells were resuspended in 10 ml TES buffer (10 mM Tris-HCl, 10 mM EDTA, 10 mM NaCl, pH8) and treated with 200 μl of lysozyme/mutanolysin mixture (4:1, lysozyme 10 mg/ml mutanolysin 1 mg/ml) for 30 minutes at 37° C. The cells were then treated with 200 μl of proteinase K (at 20 mg/ml) and 200 μl of RNase (both 10 mg/ml) and incubated for one hour at 65° C. Finally the cells were treated with 2 ml of 10% SDS and incubated for 15 minutes at 65° C. 12 ml of phenol/chloroform were added and the extraction was repeated until the water phase could easily be separated from the interphase. The genomic DNA was precipitated with isopropanol and resuspended in 10 mM Tris-HCl-1 mM EDTA (pH8). The genomic DNA was then digested with restriction enzymes, ligated into pSP72 digested with the same enzymes and treated with alkaline phosphatase. Digestion of B. bifidum genomic DNA was performed using EcoRI, PstI, BamHI, SmaI and KpnI. Ligation mixtures were used to transform E. coli DH5a and β-galactosidase positive clones were identified as blue colonies on X-Gal-containing plates.

Vector DNA Preparation

The vector used for cloning and expression throughout this study was the pSP72 (Promega, UK) (Krieg, P. A. and Melton, D. A. (1987). In vitro RNA synthesis with SP6 RNA polymerase. *Methods in Enzymology.* 155: 397-415).

This vector was chosen due to the lack of complementing activity of the α-fragment of β-galactosidase which is not encoded in pSP72. This vector does not carry the short segment of *E. coli* DNA containing the regulatory sequence and the coding information for the first 146 amino acids of β-galactosidase which in combination with *E. coli* strains (ie DH5a) which express the carboxy-terminal portion of this β-galactosidase is giving an active β-galactosidase (α-complementation).

The vector was digested with the following restriction enzymes: PstI, BamHI, HindIII, SmaI, KpnI and EcoRI according to the manufacturer instructions using a tenfold excess of enzyme over DNA (enzyme units: μgr DNA equal to ten units of enzyme per one μgr of plasmid DNA or ten enzyme units per 0.5 μmol of plasmid DNA). After enzyme heat inactivation (20 min at 65° C.) the restriction patterns were analysed by horizontal gel electrophoresis analysis. The presence of a single fragment in the gel indicated the complete vector digestion and the single restriction digestion of it.

The sufficient digestion of the vector was tested also by transforming unligated molecules into competent *E. coli* DH5a cells. The number of formed colonies on LB agar plates supplemented with ampicillin (100 μgr/ml) was an indicator of the undigested molecules and the expected background during the subsequent experiments.

The vectors were further dephosphorylated with calf intestinal alkaline phosphatase CIAP (Promega, Southampton, UK) according to the manufacturer instructions. The efficiency of the treatment was tested by ligation (with Bacteriophage T4 DNA ligase according to manufacturer instructions) following transformation into DH5a cells. The number of formed colonies showed the number of recircularised molecules (non cloned vector) and a subtraction of the above with the formed colonies without CIAP vector treatment showed the number of non dephosphorylated vectors.

Genomic DNA Library Construction

Genomic DNA was partially digested with six restriction enzymes that recognise frequently occurring hexa-nucleotide sequences within prokaryotic DNA. EcoRI, BamHI, PstI, KpnI, SmaI and HindIII are type II restriction endonucleases specifically recognizing the sequences 5'G/AATTC'3, 5'G/GATCC'3, 5'CTGCA/G'3, 5'GGTAC/C3', 5'CCC/GGG3' and 5'A/AGCTT3' respectively, and make double-strand breaks within these sequences generating 5'overhangs of four nucleotides, AATT, GATC, AGCT for EcoRI, BamHI and Hind III respectively, and 3' overhangs, ACGT,GTAC for PstI and KpnI respectively and blunt ends for SmaI.

All these enzymes were active and able to cleave DNA only in the presence of divalent magnesium ions. These ions were the only required cofactor.

Restriction Digestion of DNA.

All restriction digestions of the genomic DNA samples were incubated for 2 hours at 37° C. and finally heat inactivated at 65° C. for 20 minutes. The reactions were then cooled at room temperature and the appropriate amount of loading buffer was added, followed by gentle mixing with a sealed glass capillary. The solutions then were loaded into wells of a 0.8% agarose gel (power supply 4-5 volts/cm for 14-16 hours) and the size of the digested DNA was estimated with that of 1 kbp DNA standards (Promega, UK) (Sambrook J. Molecular Cloning: A Laboratory Manual (2002)).

Purification of the Fragments Generated after Restriction Digestion.

Fragment purification from the reaction mixtures and the agarose gels was done by using the QIAEX gel extraction kit from Qiagen (West Sussex, UK). Protocols are described with details in the manufacturer's manual.

DNA Ligation and Transformation

After purification of the DNA fragments with the Qiaex gel extraction kit, they were ligated with CLAP-treated pSP72 vector. For ligation, appropriate amounts of DNA were transferred to sterile 0.5 ml microfuge tubes as shown in Table 1.

TABLE 1

Ligation mixtures.

| Tube | DNA |
|---|---|
| A | Vector (15 fmoles [~29.7 ng]) |
| B | Vector (15 fmoles ~29.7 ng DNA) plus insert (foreign 15 fmoles ~69.3 ng) |
| C | pUC control (0.056 fmoles [~100 pg]) |

The molar ratio of plasmid DNA vector to insert DNA fragment should be ~1:1 in the ligation raction. The final DNA concentration should be ~10 ng/μl.
Tube A shows the number of self-ligated vector DNA which must be subtracted form the total number of transformants after transformation.
Tube B shows the ligation of the vector with the DNA fragments and tube C shows the control in order the transformation efficiency to be calculated.

Before each ligation the DNA fragments were warmed at 45° C. for 5 minutes to melt any cohesive termini that reannealed during fragment preparation. A molar ratio of vector:insert DNA of 1:1 was chosen for all ligation reactions and the reaction assembly was done according to Promega's instructions.

To tubes A and B 1.0 μl of 10× ligation buffer and 0.5 Weiss units of T4 DNA ligase (Promega, UK) were added and the ligation volume was adjusted to 10 μl with molecular biology grade water. To tubes C 1.0 μl of 10× ligation buffer were added and the ligation volume was adjusted to 10 μl with molecular biology grade water.

DNA fragments were added to the tubes together with the water and then warmed to 45° C. for 5 minutes to melt any cohesive termini that were reannealed during preparation. The DNA was chilled to 0° C. before the remainder of the ligation reagents were added and the reaction mixtures were incubated overnight at 16° C. (Sambrook and Russell, 2002).

After ethanol precipitation and purification of the ligated fragments (in order to remove the ligation mixture which causes a reduction of the transformation efficiency) transformations were performed according to Hanahan instructions. ~50 ng of ligated DNA in 5 μl solution was added to 100 μl of competent DH5a cells. After heat treatment and expression of the ampicillin resistance gene the cells were spread over the surface of LB plates containing ampicillin (100 μgr/ml), X-β-Gal (40 μl of 2% X-β-Gal) and IPTG (7 μl of 20% IPTG).

The number of transformants from each ligation reaction was measured. The number of transformants commonly obtained from tube C was $2 \times 10^5$-$1 \times 10^6$ cfu/μg whereas from tube A was 500-600 cfu/μg. The number of transformants in tube A was an indication of the efficient treatment of the vector DNA. The number of transformants in tube B was in a range from $2$-$4 \times 10^4$ cfu/μg.

Number of Transformants

Ligation mixtures with PstI chromosomal DNA gave rise to 13 β-galactosidase positive clones out of ~2500 screeened transformants whereas with BamHI gave rise to 7 positive clones (~1500 scr. transformants), EcoRI gave rise to 3 positive clones (~1300 scr. transformants), KpnI gave rise to 7 positive clones (~2000 scr. transformants), SmaI gave rise to 3 positive clones (~1600 scr. transformants) and HindIII gave rise to 2 positive clones (~1200 scr. transformants).

Positive Clone Digestion

In order to identify the different β-galactosidase genes, the plasmids isolated from the positive clones were digested according to the following table;

|  | Samples | Enzymes |
|---|---|---|
| 1st Digestion | pB1, pB2, pB3, pB4, pB5, pB6, pB7 | BamHI |
| 2nd Digestion | pP1, pP2, pP3, pP4, pP5, pP6, pP7, pP8, pP9, pP10, pP11 | PstI |
| 3rd Digestion | pP12, pP13, pP14 | PstI |
| 4th Digestion | pE1, pE2, pE3 | EcoRI |
| 5th Digestion | pP1, pP12, pB1, pP2, pE1, pE2, pE3 ... | PstI and EcoRI |
| 6th Digestion | pS1, pS2, pS3 | SmaI |
| 7th Digestion | pP1, pP12, pB1, pP2, pS1, pS2, pS3 | PstI and SmaI |
| 8th Digestion | pK1, pK2, pK3, pK4, pK5, pK6, pK7 | KpnI |
| 9th Digestion | pP1, pP12, pB1, pP2, pK1, pK2, pK3, pK4, pK5, pK6, pK7 | PstI and KpnI |

The first letter (p) indicates plasmid and the insert gene whereas the second letter (P, B, E, S, K) indicates the restriction enzyme that was used for isolation of the respective clone from the genomic DNA.

Gel electrophoresis analysis of the generated fragments after digestion showed that plasmids pB1, pP1, pP2 and pP11 each have an insert which encodes a different β-galactosidase. The clones containing P2 were used for further analysis.

DNA Sequencing

DNA sequencing was performed with the dideoxy chain-termination method of Sanger by using the BigDye Terminator v.3.0 cycle sequencing kit (Applied Biosystems, USA) and analysed with the ABI Prism 3100, a fluorescence-based DNA analysis system incorporating capillary electrophoresis.

The 5'- and 3'-ends of the insert DNA fragments were sequenced with vector specific primers. The inserts were further sequenced by using the Genome Priming System (GPS-1) (New England Biolabs, Uk). GPS-1 is a TN7 transposon-based in vitro system which uses TnsABC Transposase to insert Transposon randomly into the DNA target. The donor: target DNA mass ratio of 1:4 was used according to the manufacturer instructions. The number of isolated plasmids for sequencing after insertion of the Transprimer into the target plasmid was 25. This number was calculated according to the manufacturer instructions and it assumes a 5-fold depth of coverage.

Due to the long nucleotide sequence of pP2 plasmid in which protein P2 was encoded, only the part which contained the β-galactosidase gene was chosen to be sequenced. The enzyme inactivated after insertion of the transposase insert at a relative position of 172 bp of the sequenced fragment indicated that the start codon was upstream of this position. Similarly, insertion of insert at position 2882 bp completely eliminated the enzyme activity indicating that the stop codon existed downstream of this position. Moreover, the enzyme activity was eliminated completely with insertion of inserts at positions 262 bp, 331 bp, 375 bp, 621 bp, 866 bp, 1348 bp, 1358 bp, 1394 bp, 1513 bp, 1704 bp, 2128 bp, 2519 bp in respect of the first nucleotide that has been sequenced.

Analysis of the N-terminal domain with SignalIP and PSORT software, did not show any signal peptide, indicating that P2 is not secreted extracellularly.

The sequencing reaction mix contained approximately 400-600 ng plasmid DNA, 3.2 pmol of primer solution and 4 μl of BigDye Terminator solution.

Open Reading Frame Identification

The open reading frame (ORF) of P2 was located by using the ORF finder from NCBI web address http://www.ncbi.nlm.nih.gov/gorf/gorf.html). The bacterial genetic code was used and the frame length was determined to be 100 bp. The nucleotide sequence was translated in all six possible frames and an open reading frame of 738 amino acids encoding a putative β-galactosidase was identified (The translation is shown in FIG. 2).

EXAMPLE 2

Synthesis with the β-Galactosidase Cloned Enzyme Isolated from *Bifidobacterium bifidum* NCIMB 41171 in *E. coli* Host (StrainDH5a)

The following described synthesis, unless otherwise stated, was performed with the whole *E. coli* DH5a host cells after treatment of the *E. coli* biomass (collected by centrifugation at 10,000 g) with toluene at a concentration of 2000 ppm in order to increase cell permeability and also to render the cells non-viable by destroying their cytoplasmic membrane. The *E-coli* biomass was prepared as described in Example 1 under "*E coli* strains".

Synthesis with Cloned Enzyme

Synthesis with the β-galactosidase was performed at a substrate concentration of 40% (w/w) initial lactose concentration. The synthesis solution was prepared in 0.1 M phosphate buffer at pH 6.0 containing additional 1 g/l Tween 80 polyoxyethylene (20) sorbiton monooleate). Synthesis was performed at 40° C. in shaking waterbath at 150 rpm. The pH optimum for the specific enzyme was chosen based on activity measurements (using o-nitrophenyl-β-D-galactopyranoside as substrate) of a specific enzymatic preparation at varying pH values.

For galactooligosaccharide synthesis 2 ml of cell lysate supernatant were used (after disruption of the *E. coli* cells by French press) with 8 g of 50% (w/w) lactose in order to give a final substrate concentration of 40% (w/w). This enzymatic preparation had an activity of 735 U/ml.

Figure 4:
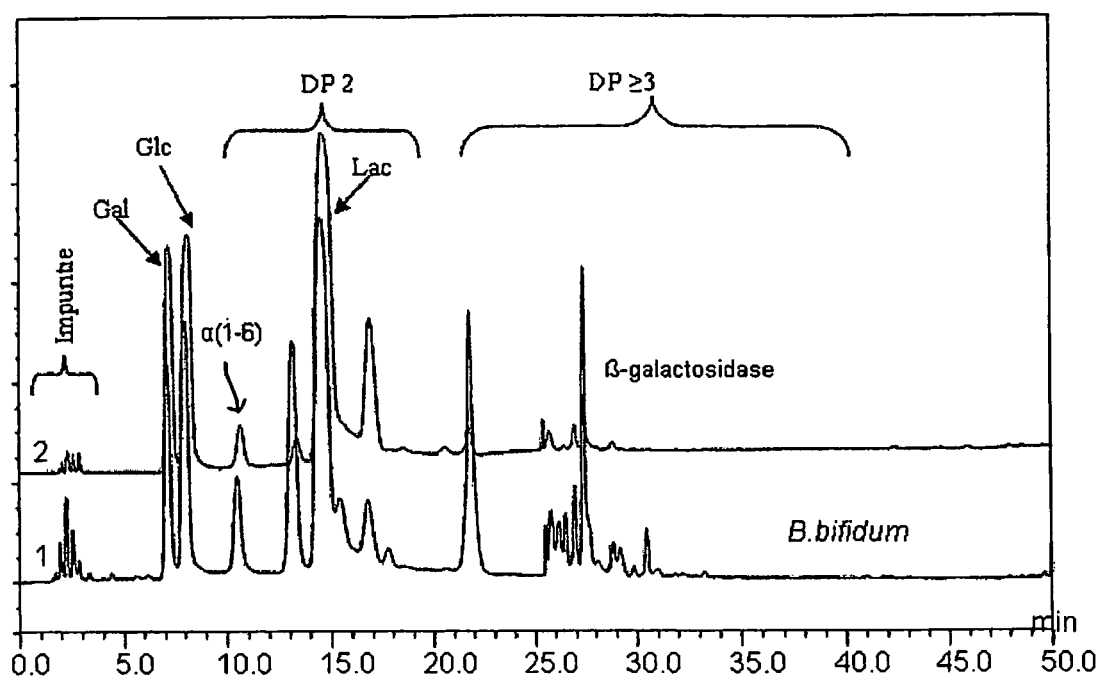
FIG. 4 shows a high performance anion exchange chromatogram of the galactooligosaccharide mixture synthesized by the β-galactosidase from B. bifidum NCIMB 41171 using 40% (w/w) lactose in O.1 M phosphate buffer at pH 6.0 as substrate (Glc=glucose, Gal=galactose, Lac=lactose, α(1-6)= galactobiose, DP=degree of polymerisation).

The concentrations of the different sugars present in the mixture during synthesis are shown in FIG. 3. High performance anion exchange chromatography coupled with pulsed amperometric detection (HPAEC-PAD) chromatograms of galactooligosaccharide mixtures synthesized by the β-galactosidase cloned from *B. bifidum* NCIMB 41171 are shown in FIG. 4. The galactooligosaccharide mixture sugar concentrations at the optimum synthesis time point are shown in table 1.

TABLE 1

Carbohydrate composition of galactooligosaccharide synthesis at 40% (w/w) initial lactose concentration at the time point where maximum oligosaccharide concentration was observed.

| Synthesis Init. Subst. % (w/w) | GOS DP ≥ 3 | GOS DP = 2 | Lac | Glc | Gal |
|---|---|---|---|---|---|
|  | Concentration (% of total sugars) | | | | |
| 40 | 8.82 | 16.25 | 39.40 | 20.76 | 14.85 |

Lac: Lactose, Glc: glucose, Gal: galactose, DP: degree of polymerisation

The invention claimed is:

1. An isolated β-galactosidase encoded by a DNA sequence, wherein the DNA sequence encodes a protein with the amino acid sequence as set forth in SEQ. ID. NO: 2.

2. An isolated β-galactosidase comprising the full length amino acid sequence as set forth in SEQ. ID. NO: 2.

3. An isolated β-galactosidase consisting of the full length amino acid sequence as set forth in SEQ. ID. NO: 2.

* * * * *

SEQUENCE LISTING

<160> NUMBER OF SEQ ID NOS: 2

<210> SEQ ID NO 1
<211> LENGTH: 4395
<212> TYPE: DNA
<213> ORGANISM: Bifidobacterium bifidum
<220> FEATURE:
<221> NAME/KEY: gene
<222> LOCATION: (1)..(4395)

<400> SEQUENCE: 1

| | | | | | | |
|---|---|---|---|---|---|---|
| tcctttagat | tggattgaaa | acttccttt | tttatgtaaa | aggatattcg | gggaaattcc | 60 |
| cttttttgaaa | atttcatgac | caaaaatccc | cttaacgtga | gttttcgttc | cactgagcgt | 120 |
| cagaccccgt | agaaaagatc | aaaggatctt | cttgagatcc | ttttttctg | cgcgtaatct | 180 |
| gctgcttgca | aacaaaaaaa | ccccgctac | cagcggtggt | ttgtttgccg | gatcaagagc | 240 |
| taccaactct | ttttccgaag | gtaactggct | tcagcagagc | gcagatacca | aatactgttc | 300 |
| ttctagtgta | gccgtagtta | ggccaccact | tcaagaactc | tgtagcaccg | cctacatacc | 360 |
| tcgctctgct | aatcctgtta | ccagtggctg | ctgccagtgg | cgataagtcg | tgtcttaccg | 420 |
| ggttggactc | aagacgatag | ttaccggata | aggcgcagcg | gtcgggctga | acgggggtt | 480 |
| cgtgcacaca | gcccagcttg | gagcgaacga | cctacaccga | actgagatac | ctacagcgtg | 540 |
| agctatgaga | aagcgccacg | cttcccgaag | ggagaaaggc | ggacaggtat | ccggtaagcg | 600 |
| gcagggtcgg | aacaggagag | cgcacgaggg | agcttccagg | gggaaacgcc | tggtatcttt | 660 |
| atagtcctgt | cgggtttcgc | cacctctgac | ttgagcgtcg | attttgtga | tgctcgtcag | 720 |
| gggggcggag | cctatggaaa | aacgccagca | acgcggcctt | tttacggttc | ctggcctttt | 780 |
| gctggccttt | tgctcacatg | ttctttcctg | cgttatcccc | tgattctgtg | gataaccgta | 840 |
| ttaccgcctt | tgagtgagct | gataccgctc | gccgcagccg | aacgaccgag | cgcagcgagt | 900 |
| cagtgagcga | ggaagcggaa | gagcgcccaa | tacgcaaacc | gcctctcccc | gcgcgttggc | 960 |
| cgattcatta | atgcaggtta | acctggctta | tcgaaattaa | tacgactcac | tatagggaga | 1020 |
| ccggcagatc | tgatatcatc | gatgaattcg | agctcggtac | ccggggatcc | tctagagtcg | 1080 |
| acctgcagaa | gtactggcag | tccggcctcg | ccgccggcgc | cgtcaaggag | tgatctcgcg | 1140 |
| ggagggccag | tgtccgcttg | cagcatgcgt | cacgttcgtc | tgacggtctt | gacgtgcgcc | 1200 |
| tagcggctgg | ccctccctac | ggaacatgta | tatgatatgg | agggacgctc | accgtgtgcg | 1260 |
| atgcgggctg | gcgcgatatg | gcaccagccc | gcatcgcatg | tcacagttga | tttttcgtcg | 1320 |
| atgcgacggt | tcggccgggg | cgtcagacaa | tgaacaagta | atggagcgga | atatgagtaa | 1380 |
| acgcagaaag | cacagttggc | cgcagccgct | gaagggcgcc | gaatcccgtc | tctggtatgg | 1440 |
| cggtgattac | aatcccgacc | aatggccgga | ggaggtctgg | gacgatgata | tccgtctgat | 1500 |
| gaagaaggcc | ggcgtcaacc | ttgtatcagt | cggcatcttc | tcatgggcga | agatcgagcc | 1560 |
| ggaggaaggc | aagtacgatt | tcgactggct | ggaccgtgcc | atcgataagc | tcggcaaggc | 1620 |
| gggcatcgct | gtagacctcg | cctccgccac | cgcctcccg | ccgatgtggc | tgacccaggc | 1680 |
| ccatccggag | gtgctgtgga | aggacgagcg | cggcgacacc | gtgtggccgg | gtgccgtga | 1740 |
| gcattggcgt | ccgacgagcc | ctgtgttccg | cgagtacgcg | ctgaacctgt | gccgtcgtat | 1800 |
| ggccgagcac | tataagggca | acccatacgt | ggtggcctgg | cacgtgagca | acgaatacgg | 1860 |
| ctgccacaac | cgcttcgact | actcggacga | cgccatgcgc | gccttccaga | agtggtgcaa | 1920 |
| gaagcgctac | aagaccatcg | acgcggtgaa | cgaggcctgg | gaacagcgt | tctgggccca | 1980 |

```
gcacatgaac gatttctccg agatcatccc gcctcgctac atcggtgacg gcaacttcat   2040
gaacccgggc aagctgctcg actacaagcg gttcagctcc gacgcgctca aggagctcta   2100
catcgccgaa cgtgacgtgc tggagtccat cacgccgggt ctgccgctga ccaccaattt   2160
catggtgtct gccggcggct cgatgcttga ctatgacgac tggggtgcgg aggtcgattt   2220
cgtctccaac gaccactact tcacgccggg cgaggaccat ttcgacgagg ttgcgtacgc   2280
cgcgtcgctg atggacggca tttcacgcaa ggaaccgtgg ttccagatgg agcattccac   2340
ctccgcggtg aattggcgtc cgatcaacta ccgtgcggag ccgggctcgg tcgtgcgcga   2400
ctccctcgcg caggtcgcta tgggcgccga tgccatctgc tatttccagt ggcgacagtc   2460
caaggccggc gcggagaagt ggcactcctc gatggtgccg catgcgggcg aggattcgca   2520
gatcttccgt gatgtgtgcg agctgggcgc cgatctggga cgtctgtccg acgagggtct   2580
gatgggcacc aagacggtca agtccaaggt cgccgtcgtg ttcgactacg agtcccagtg   2640
ggccaccgag tacaccgcga acccgaccca gcaggtcgat cattggaccg agccgttgga   2700
ttggttccgc gcgcttgccg acaacggcat caccgccgac gtggttccgg tgcggtccga   2760
ttgggattcc tacgagattg ccgtgctgcc gtgcgtgtat ttgctgtccg aagagacgag   2820
ccgcagggtt cgggagttcg tggcgaacgg cggcaagttg ttcgtgacgt actacaccgg   2880
attgagcgac gagaacgacc acatctggct tggcggctac ccgggctcga ttcgtgacgt   2940
cgtcggcgtg cgcgtcgaag agttcgcccc gatgggcaac gacatgccgg gcgcattgga   3000
tcacctcgac ctggacaatg gcacggtggc gcatgacttt gccgacgtga tcacgtccac   3060
ggccgacacg tccacggtac tggcctccta taaggcggaa cgctggaccg gcatgaacga   3120
ggtgccggcc atcgtggcca acgggtatgg cgacgggcgg accgtatatg tcggatgccg   3180
tctgggccgt caggggcttg cgaagagcct gccggcgatg ctgggttcca tgggctgtc   3240 ggacctcgcc ggtgatggcc gcgtgctgcg tgtcgaacgc gccgacgccg cggcggcgag   3300
ccgcttcgag ttcgtgttca accgcaccca tgaaccggtg accgtcgacg ttgaagggga   3360
ggccatcgcg gcttcgctcg cgcatgtcga cgacgggcgg gccaccatcg atccgacggg   3420
tgttgtcgtg ctcaggcgat aatcgttgga aacactgggc tgtaagggct taggaaaggc   3480
gtatgtttgc ggtgacacgc gacatacgcc ttatgggaaa gaaggcgctg gcgcttaccg   3540
ggctgcggcg atgctggtca gcgtcgctgc gtgcggcaac tcaagcagca gctccgctcc   3600
gaagcaggaa ggcgacgtca aggaaatcac cgtgtgggct tggggcctac gctgactcag   3660
gtggccaagg acttcaaaaa aggagaccgg catcaatgtc aacctggtga acaccggcca   3720
gggcgacaag acctgggacg agttctatca ggacgccaag aagattcaca cccttggcga   3780
caactactac atcacgtccg acaccggtgt cgccggcttc tacgactcga tgacctggct   3840
ggccagtgcg acgctgttct ccaccgaagg cgagacggtc accattaacc tgactggcgc   3900
cccgaaggtc aaggcccgcg gtatcttcgg cgactacctt ggcaagtcct acaccggcaa   3960
ccagaagctg agcgatggcg tcgccgcttt gggaacaggc tctgaaggac tacgcgaagg   4020
atcagggcta caccgtcaag taaccttcgc agtcaagcaa tctggcgtgg taatgaccgg   4080
aatacggtga ccttcggtca tcccttcctc gtgtgaaggc ccctcccctc aacagggagg   4140
ggccttcaca tatctgcccc tgttgcaacg cgcgtgtaaa ctctacgatg agcgaattct   4200
tcccgacaca tcgagcacgc taaggagatg acatgacgat atcggcacgg ttgtggcggc   4260
tgcacctgca tatctttgtg ttgctcaaga tctgtgagat gacactggca gcacgcctcc   4320
agcgcgccgc cggacacgcg caccctcatc accgaatgga cggggaccca tatcatgacg   4380
```
actctgatcg ccaat                                                                       4395

<210> SEQ ID NO 2
<211> LENGTH: 738
<212> TYPE: PRT
<213> ORGANISM: Bifidobacterium bifidum
<220> FEATURE:
<221> NAME/KEY: CHAIN
<222> LOCATION: (1)..(738)

<400> SEQUENCE: 2

Met Tyr Met Ile Trp Arg Asp Ala His Arg Val Arg Cys Gly Leu Ala
1               5                   10                  15

Arg Tyr Gly Thr Ser Pro His Arg Met Ser Gln Leu Ile Phe Arg Arg
            20                  25                  30

Cys Asp Gly Ser Ala Gly Ala Ser Asp Asn Glu Gln Val Met Glu Arg
        35                  40                  45

Asn Met Ser Lys Arg Arg Lys His Ser Trp Pro Gln Pro Leu Lys Gly
    50                  55                  60

Ala Glu Ser Arg Leu Trp Tyr Gly Gly Asp Tyr Asn Pro Asp Gln Trp
65                  70                  75                  80

Pro Glu Glu Val Trp Asp Asp Ile Arg Leu Met Lys Lys Ala Gly
                85                  90                  95

Val Asn Leu Val Ser Val Gly Ile Phe Ser Trp Ala Lys Ile Glu Pro
            100                 105                 110

Glu Glu Gly Lys Tyr Asp Phe Asp Trp Leu Asp Arg Ala Ile Asp Lys
        115                 120                 125

Leu Gly Lys Ala Gly Ile Ala Val Asp Leu Ala Ser Ala Thr Ala Ser
    130                 135                 140

Pro Pro Met Trp Leu Thr Gln Ala His Pro Glu Val Leu Trp Lys Asp
145                 150                 155                 160

Glu Arg Gly Asp Thr Val Trp Pro Gly Ala Arg Glu His Trp Arg Pro
                165                 170                 175

Thr Ser Pro Val Phe Arg Glu Tyr Ala Leu Asn Leu Cys Arg Arg Met
            180                 185                 190

Ala Glu His Tyr Lys Gly Asn Pro Tyr Val Val Ala Trp His Val Ser
        195                 200                 205

Asn Glu Tyr Gly Cys His Asn Arg Phe Asp Tyr Ser Asp Ala Met
    210                 215                 220

Arg Ala Phe Gln Lys Trp Cys Lys Lys Arg Tyr Lys Thr Ile Asp Ala
225                 230                 235                 240

Val Asn Glu Ala Trp Gly Thr Ala Phe Trp Ala Gln His Met Asn Asp
                245                 250                 255

Phe Ser Glu Ile Ile Pro Pro Arg Tyr Ile Gly Asp Gly Asn Phe Met
            260                 265                 270

Asn Pro Gly Lys Leu Leu Asp Tyr Lys Arg Phe Ser Ser Asp Ala Leu
        275                 280                 285

Lys Glu Leu Tyr Ile Ala Glu Arg Asp Val Leu Glu Ser Ile Thr Pro
    290                 295                 300

Gly Leu Pro Leu Thr Thr Asn Phe Met Val Ser Ala Gly Ser Met
305                 310                 315                 320

Leu Asp Tyr Asp Asp Trp Gly Ala Glu Val Asp Phe Val Ser Asn Asp
                325                 330                 335

His Tyr Phe Thr Pro Gly Glu Asp His Phe Asp Glu Val Ala Tyr Ala
            340                 345                 350

-continued

Ala Ser Leu Met Asp Gly Ile Ser Arg Lys Glu Pro Trp Phe Gln Met
         355                 360                 365

Glu His Ser Thr Ser Ala Val Asn Trp Arg Pro Ile Asn Tyr Arg Ala
    370                 375                 380

Glu Pro Gly Ser Val Val Arg Asp Ser Leu Ala Gln Val Ala Met Gly
385                 390                 395                 400

Ala Asp Ala Ile Cys Tyr Phe Gln Trp Arg Gln Ser Lys Ala Gly Ala
                405                 410                 415

Glu Lys Trp His Ser Ser Met Val Pro His Ala Gly Glu Asp Ser Gln
            420                 425                 430

Ile Phe Arg Asp Val Cys Glu Leu Gly Ala Asp Leu Gly Arg Leu Ser
        435                 440                 445

Asp Glu Gly Leu Met Gly Thr Lys Thr Val Lys Ser Lys Val Ala Val
    450                 455                 460

Val Phe Asp Tyr Glu Ser Gln Trp Ala Thr Glu Tyr Thr Ala Asn Pro
465                 470                 475                 480

Thr Gln Gln Val Asp His Trp Thr Glu Pro Leu Asp Trp Phe Arg Ala
                485                 490                 495

Leu Ala Asp Asn Gly Ile Thr Ala Asp Val Pro Val Arg Ser Asp
            500                 505                 510

Trp Asp Ser Tyr Glu Ile Ala Val Leu Pro Cys Val Tyr Leu Leu Ser
        515                 520                 525

Glu Glu Thr Ser Arg Arg Val Arg Glu Phe Val Ala Asn Gly Gly Lys
    530                 535                 540

Leu Phe Val Thr Tyr Tyr Thr Gly Leu Ser Asp Glu Asn Asp His Ile
545                 550                 555                 560

Trp Leu Gly Gly Tyr Pro Gly Ser Ile Arg Asp Val Val Gly Val Arg
                565                 570                 575

Val Glu Glu Phe Ala Pro Met Gly Asn Asp Met Pro Gly Ala Leu Asp
            580                 585                 590

His Leu Asp Leu Asp Asn Gly Thr Val Ala His Asp Phe Ala Asp Val
        595                 600                 605

Ile Thr Ser Thr Ala Asp Thr Ser Thr Val Leu Ala Ser Tyr Lys Ala
    610                 615                 620

Glu Arg Trp Thr Gly Met Asn Glu Val Pro Ala Ile Val Ala Asn Gly
625                 630                 635                 640

Tyr Gly Asp Gly Arg Thr Val Tyr Val Gly Cys Arg Leu Gly Arg Gln
                645                 650                 655

Gly Leu Ala Lys Ser Leu Pro Ala Met Leu Gly Ser Met Gly Leu Ser
            660                 665                 670

Asp Leu Ala Gly Asp Gly Arg Val Leu Arg Val Glu Arg Ala Asp Ala
        675                 680                 685

Ala Ala Ala Ser Arg Phe Glu Phe Val Phe Asn Arg Thr His Glu Pro
    690                 695                 700

Val Thr Val Asp Val Glu Gly Glu Ala Ile Ala Ala Ser Leu Ala His
705                 710                 715                 720

Val Asp Asp Gly Arg Ala Thr Ile Asp Pro Thr Gly Val Val Val Leu
                725                 730                 735

Arg Arg